United States Patent
Costin

(10) Patent No.: US 6,608,051 B1
(45) Date of Patent: Aug. 19, 2003

(54) COMPOSITIONS AND METHODS FOR TREATING BLOOD

(75) Inventor: James C. Costin, Belle Mead, NJ (US)

(73) Assignee: MedPointe Healthcare Inc., Somerset, NJ (US)

( * ) Notice: Subject to any disclaimer, the term of this patent is extended or adjusted under 35 U.S.C. 154(b) by 0 days.

(21) Appl. No.: 09/522,811

(22) Filed: Mar. 10, 2000

Related U.S. Application Data

(60) Provisional application No. 60/124,233, filed on Mar. 12, 1999.

(51) Int. Cl.$^7$ ................................................ A61K 31/54
(52) U.S. Cl. .................................. 514/222.5; 514/223.2
(58) Field of Search ............................ 514/222.5, 223.2

(56) References Cited

U.S. PATENT DOCUMENTS 6,166,007 A * 12/2000 Sodemann ............... 514/222.5

* cited by examiner

Primary Examiner—Russell Travers
Assistant Examiner—Shenjun Wang
(74) Attorney, Agent, or Firm—Elliot M. Olstein; Raymond E. Stauffer

(57) ABSTRACT

A blood collection system and method are disclosed in which taurolidine, a neutralizing agent for pathogens is added to the blood collected in standard blood bags. The taurolidine agent may be prepositioned in the collection bag prior to the collection of blood or alternatively the taurolidine may be added after the collection of blood has been completed.

3 Claims, No Drawings

COMPOSITIONS AND METHODS FOR TREATING BLOOD

This application is a continuation-in-part of Provisional patent application Ser. No. 60/124,233 filed Mar. 12, 1999.

The present invention relates to novel compositions and their use. In particular, this invention relates to the use of 4,4'-methylenebis(tetrahydro-1,2,4-thiadiazine)-1,1,1',1',-tetraoxide, commonly known as taurolidine, as a neutralizing agent in the destruction of blood-borne pathogens during the blood collection and storage process. In solution, taurolidine is present in equilibrium with taurultam and methyloltaurultam.

More particularly, the present invention relates to a sterile blood collection system for transfusion which includes the addition of taurolidine to eliminate pathogens from the collected blood, especially pathogens associated with sexually transmitted diseases such as the AIDS virus, syphilis, gonorrhea, genital herpes simplex, and the like.

According to recent studies, it is estimated that between one and two million people are seropositive in the United States for HTLV-III virus and are most probably carriers that can transmit the virus. Because of the increased prevalence of the HTLV-III virus in the general population and its long incubation period of up to seven years. AIDS-related transfusions are likely to be implicated in more and more cases. The above mentioned studies reveal that current tests used to screen blood donors may reduce AIDS-related transfusions but are far from eliminating them.

Researchers at the Centers for Disease Control reported that "The epidemiologic pattern of transmission of AIDS is strikingly analogous to that of Hepatitis B, e.g. from person to person, through sexual contact and through exposure to blood and its products" (D. Peter Drotman, JAMA, Aug. 23–30, 1985-Vol 254, No. 8, Questions and Answers, page 1085). According to the Technical Manual of the American Association of Blood Banks, Ninth edition, 1985 page 349: "Transfusion-associated Hepatitis B decreased since blood banks switched to predominately volunteer blood and adopted mandatory Hepatitis B surface antigen (HBsAg) screening of all donors. However, despite the most sensitive tests for HBsAg detection, occasional cases of Hepatitis B continue to occur after transfusion." Clearly, more effective techniques than screening tests are needed to avoid the spread of life-threatening pathogens such as HTLV-III through transfused blood.

According to current transfusion practice, blood is collected as whole blood containing all the blood components: Plasma, Packed Red Cells, Platelets, White Cells (Leukocytes) and coagulation factors. Using different centrifugation protocols, the whole blood can than be divided into its components.

Often, at least two blood components are transfused to different patients from a single blood unit. Whole blood contains in general 40% packed red cells and 60% plasma. Once the packed red cells are separated, the blood becomes very thick and is usually diluted before transfusion.

According to the Food and Drug Administration (FDA) regulations, once the whole blood unit is collected, it is considered a closed (sterile) system and can be stored for up to seven weeks depending on the anticoagulant and preservative used.

The whole blood can be manipulated within the different bags of the original unit but no additional bag can be added. Once an additional bag is connected or a sample taken from the main blood bag, the system is considered opened and the blood has to be transfused within 24 hours or be discarded.

DESCRIPTION OF THE INVENTION

The present invention is directed to a composition and method for preventing disease-related transfusions, especially the transmission of AIDS. Conventional approaches deal with screening donors to prevent the transmission of diseases. The present invention is directed to preventing disease-related transfusions, even from infected blood units, by neutralizing the virus with taurolidine after collecting the blood at a temperature ranging from 1 to 37 degree centigrade, preferably at room temperature, from the donor and before infusing it to patients.

The present invention provides a new, sterile, ready-to-use system for collecting blood using taurolidine as a neutralizing agent in a closed system. The blood will be ready for transfusion after the taurolidine is introduced without the need for one or more standard washing step(s) to dilute and/or remove the neutralizing agent.

The taurolidine can be separated from the inside of the standard blood collection bag by different devices used in standard blood collection units. The taurolidine can then be introduced after the blood collection and incubated for a period of time. The standard 450 ml blood container is defined as a container where the blood is first collected into the prepositioned 63 ml anticoagulant to hold between 405 ml and 495 ml (average 450 ml) of blood.

The taurolidine in the container can be either a solution or a powder separated from a reconstitution solution, with both contained in the container. The taurolidine can be reconstituted before introducing it into the 450 ml bag to mix with the whole blood. Alternatively, the taurolidine can be added directly to the blood collection bag as a powder and reconstituted by mixing it with either the transfused blood itself or liquid anticoagulant.

The taurolidine should itself be buffered to the pH of the collected blood, i.e. between 7.5 and 7.4 and can, advantageously contain substances that increase the cellular permeability for the neutralizing agent such as dimethylsulfoxide and glycerol.

Standard blood transfusion equipment also may contain several satellite bags which are connected to the primary 450 ml blood collection bag. These satellite bags, which may be the same size or smaller than the primary bag, can be used to hold blood components such as platelets, leukocytes, plasma, blood diluents, blood preservatives or whole blood. The taurolidine neutralizing agent of the invention can also be added to one of these satellite bags by means of a small attached container or pre-positioned within any bag connected to the primary collection bag in the manner discussed above or prepositioned in the 450 ml bag.

The present invention, accordingly provides, a new, ready to use, blood collection unit which can be any of the already commercially available units with taurolidine as a neutralizing agent for pathogens such as the HTLV-III virus.

The blood collection system of the present invention comprises commercially available closed blood collection bags with separate feed and exit lines into which an amount of taurolidine together with compatible anticoagulants and preservatives has been introduced which is sufficient to neutralize any pathogens present in the collected blood.

The taurolidine compositions suitable for introduction into the blood collection container may be in the form of aqueous solutions, powders or suspensions buffered to pH 7.5–7.4 collected blood and compatible with anticoagulants and preservatives usually incorporated in blood collection containers.

Taurolidine occurs as a white to off-white powder having the molecular formula $C_7H_{16}N_4O_4S_2$ and a melting point of 154–158° C.

Taurolidine's general characteristics include acceptable stability in the solid state when stored at ambient conditions, melting with decomposition at approximately 170° C. and the following solubility in aqueous solutions and organic solvents.

| | |
|---|---|
| Water | 1% at 20° C. |
| Dilute HCl | soluble |
| Dilute NaOH | soluble |
| $CHCl_3$ | insoluble |
| EtOH | sparingly soluble |
| DMF | 1 g in 2 mL/ca.60° C. |
| Acetone | 1 g in 120 mL/Boiling |
| Ethanol | 1 g in 130 mL/Boiling |
| Methanol | 1 g in 170 mL/Boiling |
| Ethyl Acetate | 1 g in 200 mL/Boiling |

A saturated solution of taurolidine in deionized water has a pH of 7.4, approximately the pH of collected blood. The apparent partition coefficient of taurolidine between octanol and water (buffered at pH 7.2) is approximately 0.13 and would therefore not be predicted to accumulate to any significant extent in fatty tissues.

The synthesis of taurolidine is covered in a number of patents including U.S. Pat. No. 3,423,408; Switzerland No. 482,713 and United Kingdom No. 1,124,285 and is carried out in five stages:

Potassium phthalimidoethane sulphonate is prepared from taurinc, phthalic anhydride, glacial acetic acid and potassium acetate;

Potassium phthalimidoethane sulphonate is then converted to phthalimidoethane sulphonylchloride by chlorination with phosphorous oxychloride;

Phthalimidoethane sulphonylchloride is reacted with ammonia to form phthalimidoethane sulphonamide;

Phthalimidoethane sulphonylchloride is reacted with hydrazine hydrate and in the subsequent hydrazinolysis to form taurinamide hydrochloride; and Taurolidine is prepared from taurinamide hydrochloride and formaldehyde.

The antimicrobial actions of taurolidine have been described in U.S. patent application Ser. No. 09/151,885 filed Sept. 11, 1998 and in U.S. Pat No. 3,423,408 and elsewhere in the literature. In addition, the following United States Patents describe various uses for and compositions containing taurolidine: U.S. Pat. No. 4,107,305, treatment of endotoxaemia; U.S. Pat. No. 4,337,251, elimination of adhesion formation as a result of surgery; U.S. Pat. No. 4,587,268, resorbable aqueous gels; U.S. Pat. No. 4,604,391, prevention of the occurrence of osteitis or osteomyelitis; U.S. Pat. No. 4,626,536, combating toxic proteins or peptides in the blood; U.S. Pat. No. 4,772,468, treatment of bone cavities; and U.S. Pat. No. 4,882,149, directed to methods for filling congenital, surgical or traumatic defects with compositions comprising natural bone mineral having absorbed therein/thereon taurolidine.

Taurolidine has been shown to be safe and well tolerated at systemic doses exceeding 40 g/day and cumulative doses up to and exceeding 300 g.

The formulations of taurolidine utilized in the present invention are sterile solutions containing 0.5%, 1.0%, 2.0% or 4.0% taurolidine.

According to the present invention there are provided pharmaceutical compositions comprising taurolidine with one or more carriers or excipients. The compositions preferably take the form of powders, sprays, solutions or suspensions.

The carriers or excipients in such compositions may, for example, be those conventional for such forms and may include gelatin, sterile water, suspending, emulsifying, dispersing, thickening or gelling agents.

The compositions of the present invention in the form of powders, solutions or suspensions, preferably contain the active substance at a concentration between 0.10 and 20.0% by weight, preferably between 0.5 and 2.0% for aqueous solutions or suspensions or up to 10% for powders.

The amounts of taurolidine introduced into the blood collection container will vary according to the concentration of pathogens in the collected blood and are adjusted such that the amount of taurolidine is sufficient to destroy the infective agents present in the collected blood and in the process the taurolidine itself is used up, thus producing a sterilized bag of blood but with no taurolidine present that could subsequently be administered to the patient receiving the blood transfusion.

The taurolidine compositions may be introduced into the blood collection container, which is usually a sealed, flexible bag, during manufacture of the container and prior to the sealing of the container or alternatively the system may include a second container connected to the blood collection container for controllably introducing taurolidine composition into the blood collection container.

Modifications and variations of the method to selectively, and in a controlled manner, inhibit specific viruses such as HIV, and use thereof in the treatment of viral infections will be obvious to those skilled in the art from the foregoing detailed description. Such modifications and variations are intended to come within the scope of the appended claims.

I claim:

1. A method for inactivating viral components in blood or blood components, obtained from a human for blood transfusion to a human patient in need thereof, comprising adding to the blood or blood components 4,4'-methylenebis-(tetrahydro-1,2,4-thiadiazine)-1,1,1',1', -tetraoxide in a concentration which is effective to inactivate the viral components in the blood components, wherein the blood or blood components is in need of such treatment.

2. The method of claim 1 wherein the blood component comprises blood mononuclear cells.

3. The method of claim 1 wherein said 4,4'-methylenebis-(tetrahydro-1,2,4-thiadiazine)-1,1,1', 1',-tetraoxide is in powder form.

* * * * *

UNITED STATES PATENT AND TRADEMARK OFFICE
CERTIFICATE OF CORRECTION

PATENT NO.    : 6,608,051 B1
DATED         : August 19, 2003
INVENTOR(S)   : Costin It is certified that error appears in the above-identified patent and that said Letters Patent is hereby corrected as shown below:

Column 4,
Line 51, after "blood" and before "components" insert -- or blood --
Line 54, after "comprises" and before "blood" insert -- peripheral --

Signed and Sealed this

Sixth Day of April, 2004

JON W. DUDAS
*Acting Director of the United States Patent and Trademark Office*